United States Patent [19]

Burrows

[11] Patent Number: 5,739,038

[45] Date of Patent: Apr. 14, 1998

[54] SPECTROMETER GAS ANALYZER SYSTEM

[75] Inventor: Donald Edward Burrows, Santa Barbara, Calif.

[73] Assignee: Anarad, Inc., Santa Barbara, Calif.

[21] Appl. No.: 686,827

[22] Filed: Jul. 26, 1996

[51] Int. Cl.$^6$ .................. G01N 33/00; G01N 21/01; G01N 21/31

[52] U.S. Cl. .................. 436/113; 436/116; 436/117; 436/118; 436/119; 436/120; 436/121; 436/122; 436/155; 436/158; 436/171; 422/83; 422/91; 422/93; 422/199

[58] Field of Search .................. 436/113, 116, 436/117, 118, 119, 120, 121, 122, 155, 158, 164, 171; 422/83, 91, 93, 174, 199

[56] References Cited

U.S. PATENT DOCUMENTS

| | | | |
|---|---|---|---|
| 2,417,321 | 3/1947 | Park et al. | 436/118 |
| 3,300,282 | 1/1967 | Risk et al. | 436/121 |
| 3,652,227 | 3/1972 | Harman, III et al. | 436/118 |
| 3,718,429 | 2/1973 | Williamson, Jr. | |
| 3,768,982 | 10/1973 | Kitzner et al. | 422/174 |
| 3,819,945 | 6/1974 | Egan et al. | |
| 3,835,322 | 9/1974 | Komatsu | 436/118 |
| 3,935,463 | 1/1976 | Jacobsen | |
| 3,967,933 | 7/1976 | Etess et al. | |
| 3,970,430 | 7/1976 | Reader et al. | |
| 4,042,333 | 8/1977 | Dell et al. | 436/116 |
| 4,069,420 | 1/1978 | Ross | |
| 4,153,837 | 5/1979 | Ross | |
| 4,221,130 | 9/1980 | Burrows | |
| 4,238,198 | 12/1980 | Swain et al. | |
| 4,306,152 | 12/1981 | Ross et al. | |
| 4,333,735 | 6/1982 | Hardy et al. | 422/91 X |
| 4,441,815 | 4/1984 | Izumi | |
| 5,015,590 | 5/1991 | Kinrade | |
| 5,084,080 | 1/1992 | Hirase et al. | 422/174 X |
| 5,246,668 | 9/1993 | MacCallum et al. | 436/113 X |
| 5,424,217 | 6/1995 | Benner et al. | 436/122 X |

FOREIGN PATENT DOCUMENTS 56-44845  4/1981  Japan .................. 436/122

OTHER PUBLICATIONS

R.S. Saltzman et al. *Air Qual. Instrum*, 1972, 1, 169–177.
K. Ito et al. *Jpn. J. Appl. Phys.* 1975, 14 *Suppl.*, 131–136.
K.E. Noll et al. "Power Generation" K.E. Noll et al. ed. Ann Arbor Science: Ann Arbor, Michigan, 1976, pp. 187–198.
D.E. Burrows *Adv. Instrum.* 1985, 40, 1357–1385.
M.D. Durham et al. *Proc. Annu. Meet —Air Waste Manage. Assoc.* 1991 Paper 91/180.1.

(List continued on next page.)

*Primary Examiner*—Arlen Soderquist
*Attorney, Agent, or Firm*—Michaelson & Wallace

[57] ABSTRACT

A gas analyzer system for providing a spectroscopic analysis of the sample gas. This analysis is accomplished by first introducing the sample gas into the inlet of the system and transporting it to a spectral analyzer. The sample gas is then spectrally analyzed and the analyzer outputs a signal indicative of a radiation intensity spectrum associated with the analyzed sample gas. A processing unit uses the analyzer signal to detect the presence of one or more prescribed gases and to determine the concentration of each of the prescribed gases in the sample gas. Next, the reacting agent is supplied to the sample gas to convert one or more gases whose presence in the sample gas cannot be detected via spectral analysis due to the masking effects other gases present in the sample gas. The masked gases are converted to secondary gases at least one of which is readily detectable via spectral analysis. This converting process occurs in the time it takes for the sample gas to transit uninterrupted through the system to the analyzer. The modified sample gas is spectrally analyzed, and the processing unit detects the presence of the masked gases and determines the concentration of each. The system may be employed to monitor certain environmental gases contained within industrial emission. In such a case, the prescribed gases are nitrogen dioxide and sulfur dioxide, and the masked gases are nitric oxide, ammonia, and hydrogen sulfide.

31 Claims, 11 Drawing Sheets

OTHER PUBLICATIONS

F.F. McElroy et al. Report EPA/600/A-93/251, 1993.

J. Leppalahti et al. *VTT Publ.* 1994, 51 pages.

R.S. Wright et al. *Air Waste* 1994, 44, 428–430.

M.G. Mennen et al. *Comm. Eur. Communities EUR* 1994, 15609, 761–766.

M.J.T. Milton et al. *Proc. SPIE–Int. Soc. Opt. Eng.* 1995, 2506, 680–688.

A.A. Adesing et al. *Int. J. Hydrogen Energy* 1995, 20, 777–783.

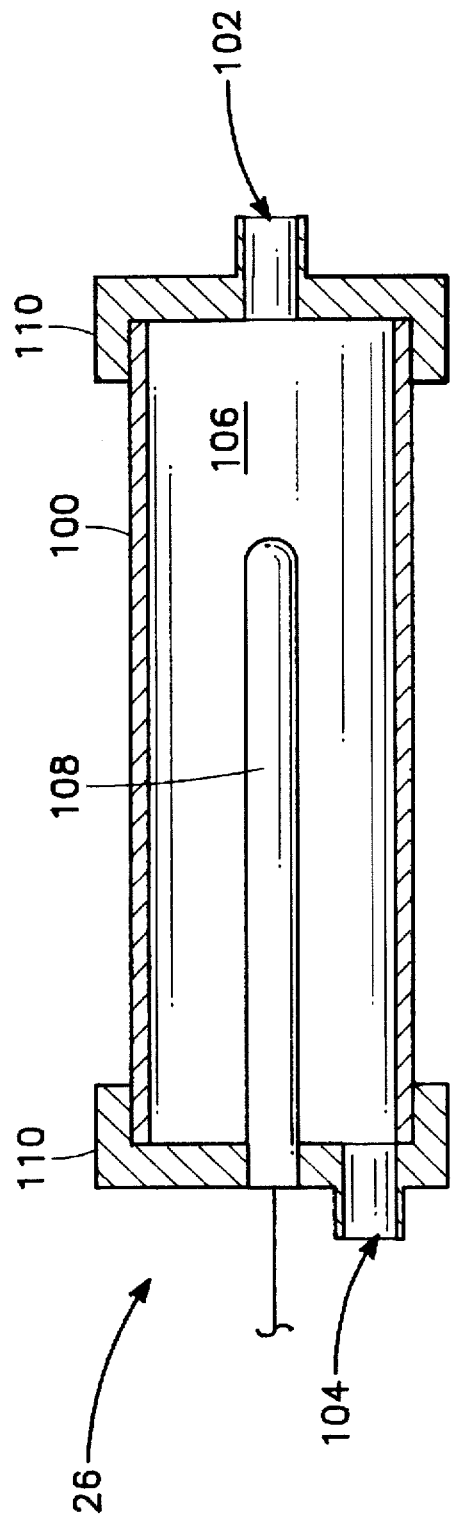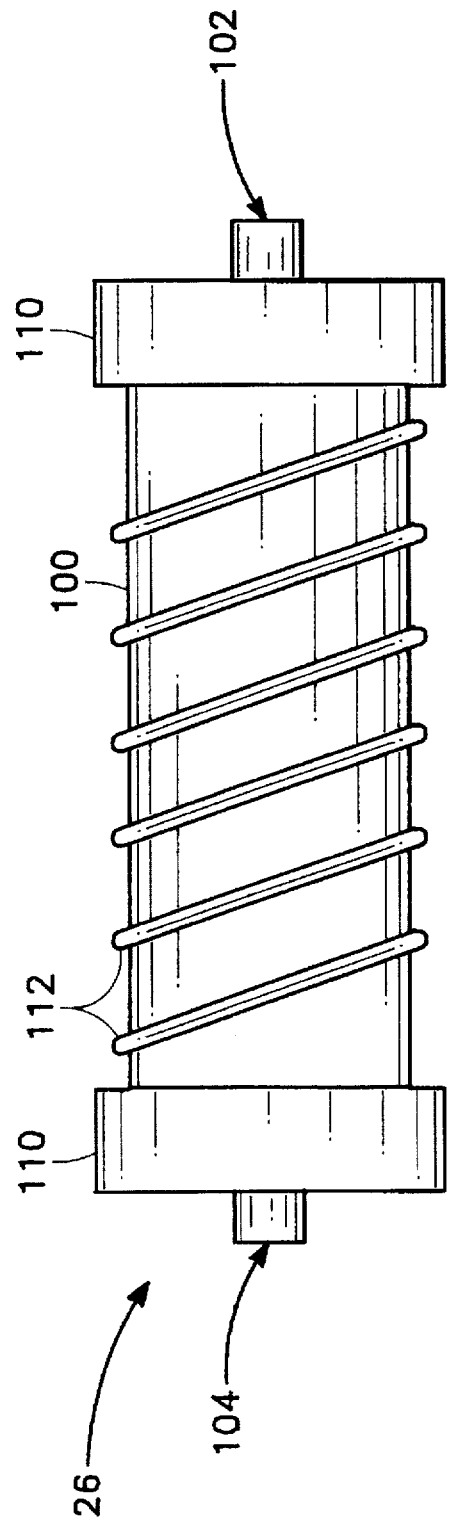
FIG. 5A
FIG. 5B

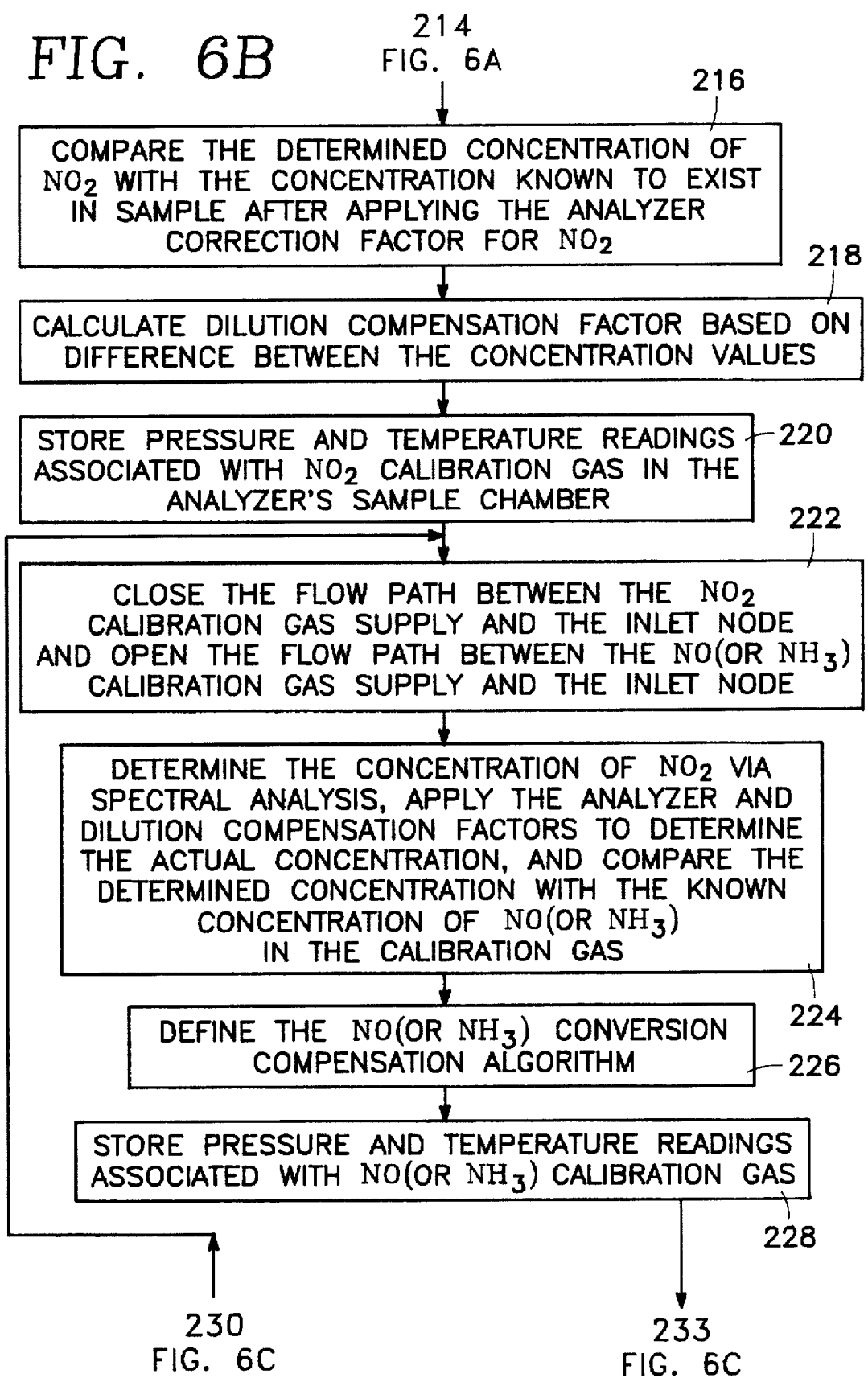

SPECTROMETER GAS ANALYZER SYSTEM

BACKGROUND

1. Technical Field

The present invention relates to spectroscopy, and in particular to a spectroscopic gas analyzer system for the analysis of gases to determine the presence and quantity of specific materials.

2. Background Art

The use of spectroscopic analysis to monitor emission of noxious materials and gases into the air is well known. For example, the gaseous emissions resulting from various industrial processes are often monitored for the presence of so-called environmental gases such as nitric oxide (NO), nitrogen dioxide ($NO_2$), ammonia ($NH_3$), hydrogen sulfide ($H_2S$), and sulfur dioxide ($SO_2$), to name a few.

It is well known that atoms and molecules absorb or emit radiation at specific frequencies. As a result, each molecular composition of matter will exhibit a unique spectral distribution pattern. This pattern constitutes the spectral signature of the particular molecular composition. Spectroscopic analysis generally involves passing a beam of polychromatic light through a gas sample and thereafter determining the specific frequencies of light absorbed by the constituents of the sample. This determination task is performed in a variety of ways. For example one well known device, a diode-array spectrophotometer, uses a polychromator to produce a spectrum corresponding to light which was passed through a gas sample. The spectrum is directed onto diode-array, where each of the diodes is dedicated to measuring a narrow band thereof. The intensity of the light impinging on each diode is sensed. The resulting intensity profile is then analyzed to determine the presence and quantity of specific gases, such as the environmental gases mentioned previously. The analysis process is performed using well known algorithms, such as the Spectral Analysis Optimization algorithm.

A problem encountered when attempting to detect the presence or quantity of a particular gas which may or may not be present in a gas sample, is that other gases may have overlapping absorption characteristics. This can result in the spectral signature of a particular gas being masked by one or more others. For example, FIG. 1 is a graph plotting absorbance against wavelength for a sample containing sulfur dioxide, ammonia, and nitric oxide in concentrations typical of industrial emissions. The absorption characteristic for each gas is shown on the graph, as well as the combined absorbance curve which would actually be detected by a spectral analyzer. As can be seen the absorbance characteristics of ammonia and nitric oxide tend to be masked by the absorbance profile of the sulfur dioxide. The combined absorbance which would be detected by a spectrometer would be the summation of the absorbances of the three gases. However, given the overshadowing absorbance of the sulfur dioxide, it is very difficult to determine with any accuracy the relative concentrations of nitric oxide and ammonia. It is even difficult to determine whether these gases are present. Even when the total absorbance at several wavelengths is analyzed, it is still difficult to distinguish and quantify the amounts of the gases present because of the masking effect of the sulfur dioxide. This presents a considerable problem because nitric oxide is seldom present without sulfur dioxide in typical emission gases. In addition, the presence of ammonia and sulfur dioxide is also common, for example, where ammonia is injected into emissions from coal-burning power plants to reduce the concentrations of other nitrogen-containing gases. Excess ammonia remaining in the emissions must typically be monitored. However, these emission also contain sulfur dioxide which masks the ammonia from spectroscopic analysis.

Heretofore, to distinguish between nitric oxide and sulfur dioxide, it has been known to react the nitric oxide with oxygen gas under heat and pressure to form nitrogen dioxide. Typically, this process involves trapping the sample gas in a chamber and injecting oxygen gas as a reactant and to increase the pressure. Finally, the temperature is increased to facilitate the conversion of the nitric oxide to nitrogen dioxide. This process typically required 5–10 minutes to complete. The advantage of converting the nitric oxide to nitrogen dioxide is that nitrogen dioxide exhibits an absorption profile which is not masked by sulfur dioxide. FIG. 2 plots absorbance against wavelength for a sample containing sulfur dioxide and nitrogen dioxide. As can be seen the two gases are easily distinguishable as their absorption peaks generally do not coincide. Although the aforementioned process works well, the conversion of the nitric oxide to nitrogen dioxide takes a significant period of time. This makes real-time analysis of an emission sample impossible. However, many environmental gas monitoring application require real time or nearly real time determination of the presence and/or concentration of gases such as nitric oxide, ammonia, or in many cases the overall concentration of nitrogen-containing gases. For example, some states have regulations requiring industrial emissions to be sampled and analyzed for such gases once every minute. Obviously, if the conversion of nitric oxide to nitrogen dioxide requires 5–10 minutes, the once-a-minute requirement could not be met.

A similar conversion process has been used to distinguish ammonia from a sample also containing sulfur dioxide. Typically, the ammonia was first converted to nitric oxide, and then to nitrogen dioxide, before the spectral analysis is performed. Previous methods for converting ammonia to nitric oxide could be performed real time, i.e. for example, flowing the sample gas containing ammonia through a heated stainless steel chamber. However, the same time-consuming process had to then be employed to convert the newly formed nitric oxide to nitrogen dioxide. Therefore, the conversion of ammonia to a gas readily distinguishable under spectral analysis could also not be performed on a real-time basis.

Thus, a need exists for a spectroscopic gas analyzer system which can provide real time or nearly real time monitoring of gaseous emission for pollutants such as ammonia and nitric oxide, or all nitrogen-containing gases including ammonia and nitric oxide, in emissions also containing sulfur dioxide.

Accordingly, it is an object of the present invention to provide a method and apparatus for the real time or nearly real time detection of the presence and quantity of specific nitrogen-containing gases, such as nitric oxide, nitrogen dioxide, and/or ammonia, taken from the gaseous emissions of an industrial process also containing sulfur dioxide.

It is another object of the present invention to provide a method and apparatus for the real time or nearly real time detection of the presence and combined quantity of nitrogen-containing gases in such an gas sample.

Another example of overlapping absorbance profiles is shown in FIG. 3. Here, hydrogen sulfide is overshadowed by the absorbance profile of sulfur dioxide and cannot easily be distinguished and quantified. Some applications require the concentration of hydrogen sulfide in industrial emission to be reported. Thus, there is also a need for a spectroscopic gas analyzer system which can provide real time or nearly real time monitoring of gaseous emission for hydrogen sulfide, whenever sulfur dioxide is present.

Accordingly, it is a further object of the present invention to provide a method and apparatus for the real time or nearly real time detection of the presence and quantity of hydrogen sulfide in a sample gas also containing sulfur dioxide.

SUMMARY

The above-described objectives are realized with the present invention which is embodied in a gas analyzer system having a sample gas inlet for introducing a sample gas, a first mixer having a first inlet into which the sample gas is fed, a first mixer supply containing a reacting agent connected to a second inlet of the first mixer so as to supply the agent thereto, and a spectral analyzer having an inlet into which the now modified sample gas is fed. The spectral analyzer outputs a signal indicative of a radiation intensity spectrum associated with the modified sample gas. A pump is responsible for transporting the gas through the system.

In operation this system provides a spectroscopic analysis of the sample gas. This is accomplished by first introducing the sample gas into the inlet of the system and transporting it to the spectral analyzer. The sample gas is then spectrally analyzed and the analyzer outputs the aforementioned signal indicative of a radiation intensity spectrum associated with the analyzed sample gas. A processing unit uses the analyzer signal to detect the presence of one or more prescribed gases and to determine the concentration of each of the prescribed gases in the sample gas. Next, the reacting agent is supplied to the mixer to convert one or more masked gases present in the sample gas which cannot be detected via spectral analysis due to the presence of the prescribed gases, to secondary gases at least one of which is readily detectable via spectral analysis. This converting process occurs in the time it takes for the sample gas to transit uninterrupted through the mixer, thus providing a real time conversion of the masked gases. The modified sample gas is spectrally analyzed, and the processing unit detects the presence of the masked gases and determines the concentration of each.

The system can be employed to monitor environmental gases such as nitrogen dioxide and nitric oxide found with industrial emissions. If so, the prescribed gas is nitrogen dioxide, the reacting agent being supplied to the first mixer is preferably ozone, the masked gas is nitric oxide, and the secondary gas is nitrogen dioxide. Thus, the concentration of nitric oxide in the sample gas is related to the increase in the detected levels of nitrogen dioxide after the first mixer is activated.

The system can also be employed to monitor ammonia in the sample gas. If so, the system also includes an ammonia reactor disposed between the sample gas inlet and the first mixer. The ammonia reactor is capable of converting gaseous ammonia to a gas comprising a quantity of nitric oxide in the time it takes for the sample gas to flow through the ammonia reactor. Therefore, once the concentration of nitrogen dioxide and nitric oxide are determined as described above, the ammonia reactor would be activated and the resulting increase in the nitrogen dioxide level is used to determine the concentration of ammonia in the sample gas.

In applications where only the total concentration of nitrogen-containing gases is required, the individual concentrations of nitrogen dioxide, nitric oxide, and ammonia would be added together to obtain the desired result. Similarly, where a combined concentration of less than all the nitrogen-containing gases is required, such as for example the combined concentration of nitrogen dioxide and nitric oxide (i.e. NOX gases), this result could also be provided by combining the individually derived concentrations for those gases.

The system can further be modified to monitor environmental gases such as sulfur dioxide and hydrogen sulfide. This is accomplished by adding a second mixer having a first inlet into which the sample gas can be fed and a second mixer supply containing an reading agent connected to a second inlet of the second mixer so as to supply the agent thereto. The second mixer also has the capability of heating the sample gas as it flows through the mixer. An inlet distribution node is also included. This inlet node has a first inlet connected to the sample gas inlet, a first outlet connected to an inlet of the ammonia reactor, and a second output connected to the first inlet of the second mixer. This inlet distribution node is capable of exclusively routing the sample gas to either the ammonia reactor or the second mixer. The modified system having the second mixer monitors the sulfur dioxide and hydrogen sulfide in the same way the system monitored nitrogen dioxide and nitric oxide. Except that the sulfur dioxide is the prescribed gas, the reacting agent is oxygen gas and the gas moving through the mixer is heated to above 1000 degrees Fahrenheit, the masked gas is hydrogen sulfide, and the secondary gas of interest is sulfur dioxide. In operation, the sulfur dioxide level is determined first, then the second mixer is activated and the resulting increase in the sulfur dioxide level caused by the conversion of hydrogen sulfide is used to determine the concentration of the hydrogen sulfide in the sample gas. In some cases the sample gas may contain sufficient quantities of oxygen so that adding more from the second mixer supply is not needed. Accordingly, in such cases the supply would not be activated and no additional oxygen would be supplied to the heated mixer.

It is noted that ozone (i.e. the preferred reacting agent employed in the first mixer) is capable of causing damage to the pump. Therefore, when ozone is used, it is preferred that the system include an ozone killer capable of converting the ozone to gases which will not damage the pump. This ozone killer would be connected between the spectral analyzer and the pump.

It is also noted that the addition of a reacting agent into the sample gas will have a diluting effect that must be compensated for in order to determine the true concentrations of the masked gases, such as nitric oxide, ammonia, and hydrogen sulfide. In addition, the spectral analyzer may have inherent inaccuracies that must also be compensated for to obtain true results. To this end the processing unit is capable of compensating for inaccuracies in the spectral analyzer and the dilution effects caused by the introduction of the reacting agent into the sample gas. The conversion of the masked gases to a secondary gas which is readily detected via spectral analysis also causes a skewing of the results because the concentration of this secondary gas will not be the same as the original concentration of the masked gas. Accordingly, the processing unit is also capable of compensating for the resultant difference between the concentration of the readily detectable gases created in the conversion process and the concentration of the masked gas in the original sample gas. Finally, as changes in the pressure and temperature over time will skew the analysis results, the processing unit is equipped with the capability to compensate for the effects of changes in the pressure and temperature of a sample gas being analyzed.

In addition to the just described benefits, other objectives and advantages of the present invention will become apparent from the detailed description which follows hereinafter when taken in conjunction with the drawing figures which accompany it.

DESCRIPTION OF THE DRAWINGS

The specific features, aspects, and advantages of the present invention will become better understood with regard to the following description, appended claims, and accompanying drawings where:

FIG. 5A is a cross-sectional view of a gas reactor in accordance with the present invention having an internal heat probe.

FIG. 5B is a side view of a gas reactor in accordance with the present invention having an external heating coil.

FIGS. 6A to 6D are block diagrams showing a method for calibrating the system of FIG. 4.

DETAILED DESCRIPTION OF THE PREFERRED EMBODIMENTS

In the following description of the preferred embodiments of the present invention, reference is made to the accompanying drawings which form a part hereof, and in which is shown by way of illustration specific embodiments in which the invention may be practiced. It is understood that other embodiments may be utilized and structural changes may be made without departing from the scope of the present invention.

Figure 1:
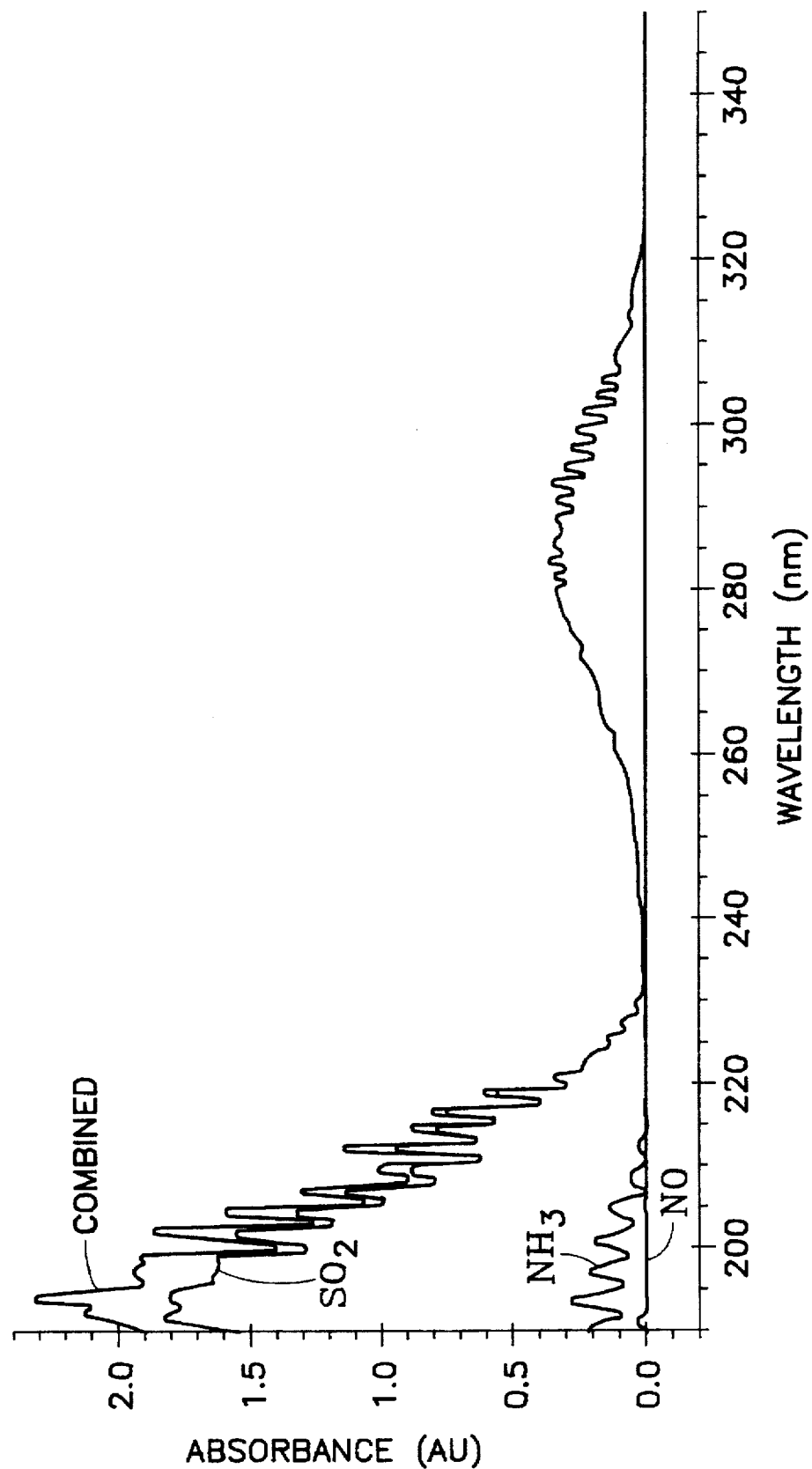
FIG. 1 is a graph plotting the absorbance of a gas containing sulfur dioxide, ammonia, and nitric oxide against wavelength. The absorbance profile for each gas is shown, as well as the combined absorbance profile for all three gases.
Figure 2:
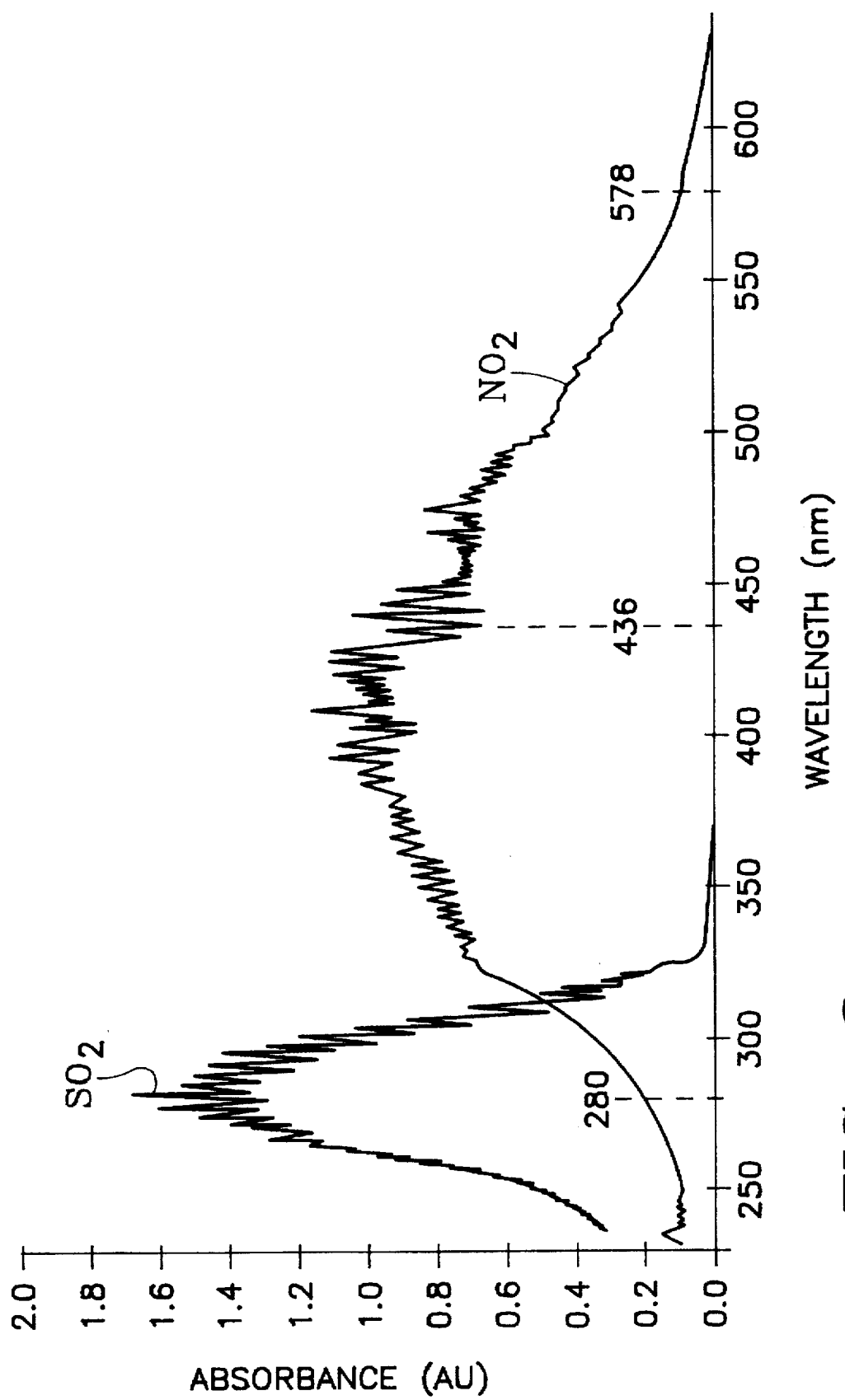
FIG. 2 is a graph plotting the absorbance of a gas containing sulfur dioxide and nitrogen dioxide against wavelength.
Figure 3:
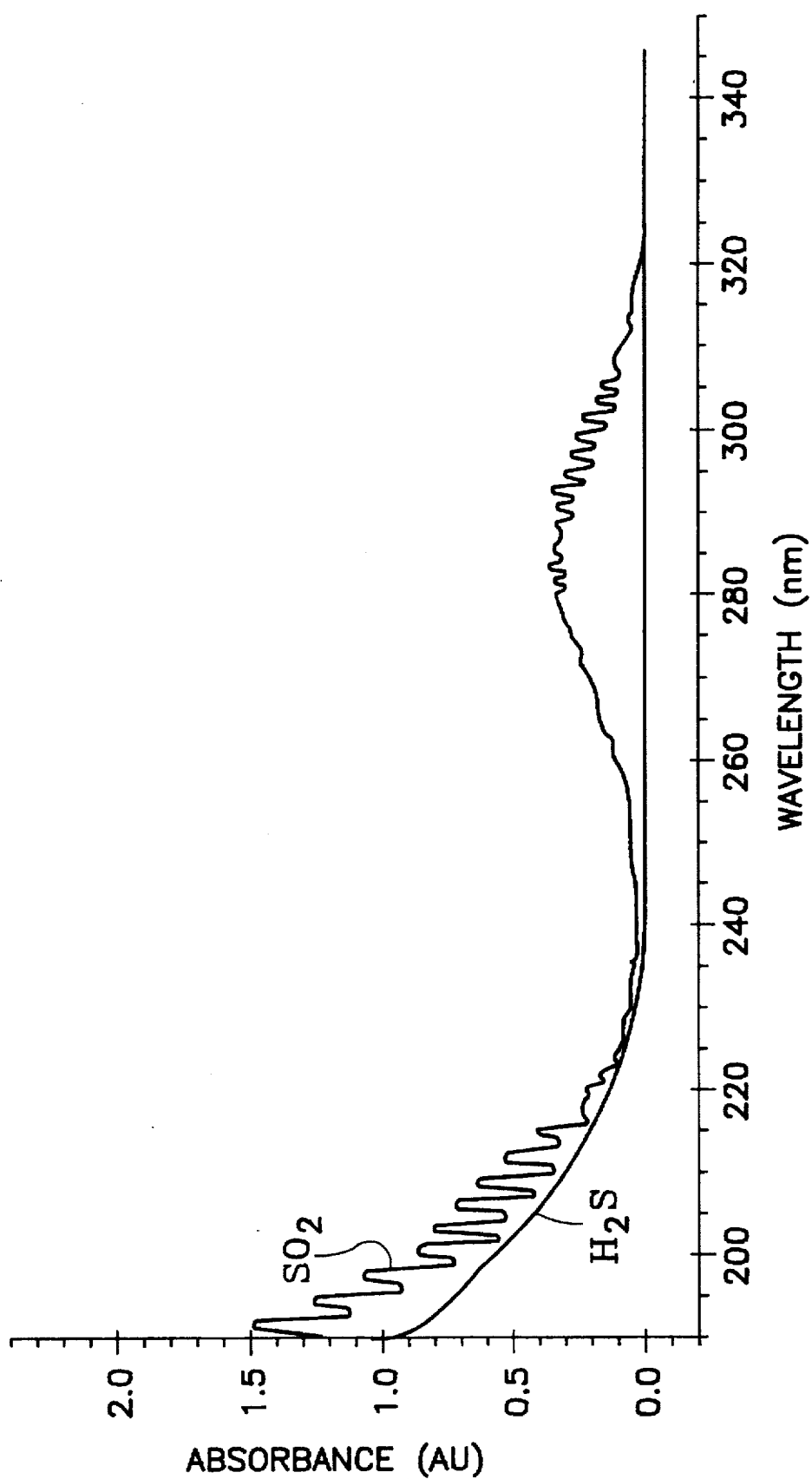
FIG. 3 is a graph plotting the absorbance of a gas containing sulfur dioxide and hydrogen sulfide against wavelength. The absorbance profile for each gas is shown, as well as the combined absorbance profile for both gases.
Figure 4:
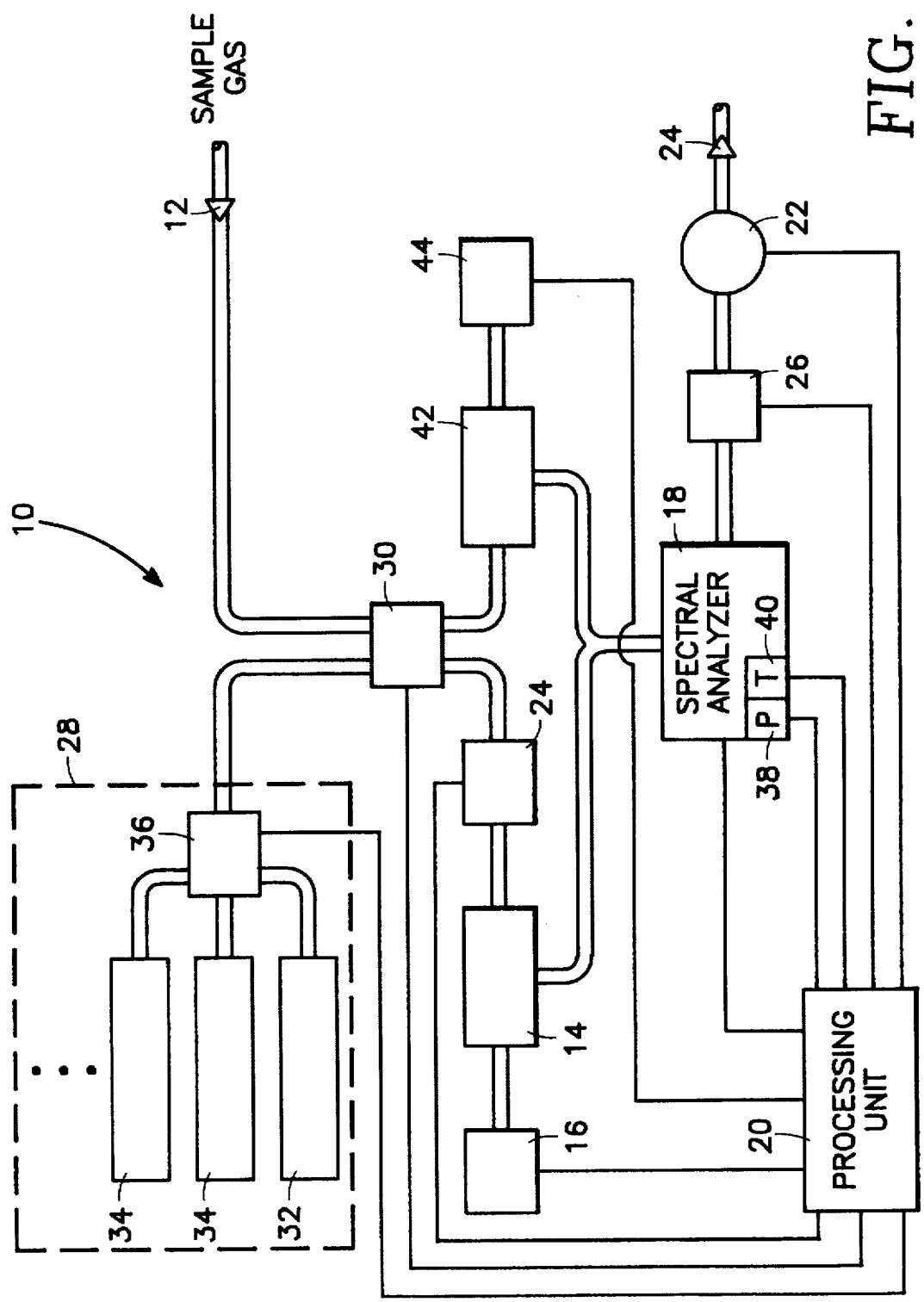
FIG. 4 is block diagram of a gas analyzer system in accordance with the present invention.

FIG. 4 shows an embodiment of the present invention in the form of a gas analyzer system 10. The system includes a gas inlet 12 that receives a sample of gas to be analyzed. The sample gas can be transmitted through a mixer 14 where a reacting agent is also introduced via the mixer supply 16. Preferably, the mixer 14 employs critical orifices operated in conjunction with a vacuum maintained inside the mixer. The orifices are sized to control the ratio of sample gas to reacting agent. The reacting agent is preferably an oxidant, namely ozone ($O_3$). Both the sample gas, as modified by the ozone, and any excess ozone, are drawn through a spectral analyzer 18. The spectral analyzer employed may be any appropriate spectroscopic device, however, a preferred analyzer would be a diode-array spectrophotometer, for example Model 8450A, manufactured by Hewlett Packard of Palo Alto, Calif. The spectral analyzer 18 is employed to provide a signal indicative of the spectral intensity profile of the modified gas sample to a processing unit 20. Preferably, this processing unit 20 takes the form of a personal computer with the appropriate interface module to convert the analyzer signal to a signal useable by the computer. The sample gas is drawn through the system by a pump 22. It is this pump 22 which creates the aforementioned vacuum in the mixer 14. An example of an appropriate pump is Model N10 manufactured by KNF of Germany. The sample gas is eventually vented through an exhaust port 24 connected to the output of the pump 22.

As described previously, the absorption characteristics of certain gases, such as nitric oxide, are masked by other gases, specifically sulfur dioxide. Thus, when nitric oxide and sulfur dioxide are both present in the gas sample being monitored, it is difficult to detect the presence and quantity of the masked nitric oxide. It is desirable to convert the nitric oxide to a proportionate quantity of nitrogen dioxide, a gas having an absorption profile which is not masked by sulfur dioxide, to make it readily detectable and quantifiable by the system 10. The nitric oxide is converted to nitrogen dioxide as it flows through the mixer 14 and mixes with the ozone. The amount of ozone introduced into the mixer 14 is chosen to ensure a substantially complete conversion of any nitric oxide to nitrogen dioxide in the time it takes for the sample gas to transit through the mixer 14. Thus, no time is wasted in conversion process, and so a real time monitoring capability for nitric oxide can be realized for the first time in a system employing spectral analysis. It is noted that other nitrogen oxide gases or NOX gases may exist in the sample gas, especially nitrous oxide ($N_2O$). Such gases may also be converted to a quantity of nitrogen dioxide by the oxidant. However, in most applications the concentrations of these other NOX gases will be so small, that any additional nitrogen dioxide created by their conversion will be negligible and will not significantly effect the determination of the concentration of nitric oxide in the sample gas.

The sample gas will typically contain unknown quantities of nitric oxide. Thus, the amount of ozone provided to the mixer 14 is also preferably sufficient to convert the maximum anticipated concentration of nitric oxide in the sample. In the case of the preferred oxidant, i.e. ozone, a flow rate of approximately 50 milliliters per minute (ml/min) is believed to be sufficient to achieve the desired conversion of the maximum amount of nitric oxide typically seen in industrial emissions (i.e. approximately 500 ppm), assuming a sample gas flow rate of about 300–500 ml/min. This assumed sample gas flow rate range corresponds to the range usually required by most spectral analyzers to provide accurate readings.

Of course, providing enough ozone to the mixer to ensure that even the highest concentrations of nitric oxide are converted to nitrogen dioxide will likely mean that excess ozone will be supplied in many cases. This excess ozone will have two impacts on the system 10. First, it will dilute the gas sample. Essentially, the quantitative results of the spectral analysis will be skewed because it will appear there is a lower concentration of a specific gas of interest (e.g. nitric oxide) in the sample gas due to the introduction of the ozone. This dilution effect is compensated for by properly calibrating the system 10, as will be discussed later in this description.

The second impact excess ozone will have on the system 10 concerns the pump 22. It is preferred that most of the system components which will come into contact with excess ozone (such as the mixer 14, spectral analyzer 18, and various valves and piping) are made of materials which are impervious to any of its deleterious effects. For example, these aforementioned system components could be made of Teflon or stainless steel, both of which will be unaffected by the ozone. However, it is anticipated that any excess ozone left in the modified sample gas could damage the pump 22. For example, commercially available pumps of the kind appropriate for use with the present system 10 (including the exemplary model identified above) typically have parts made of materials which will corrode in the presence of ozone. Specifically, pump parts such as the pump head, diaphragm, and flapper valves will come into contact with the sample gas and are typically made of materials which could be destroyed by ozone.

To prevent damage to the pump 22, it is preferred that the system 10 also include an ozone reactor or killer 26 disposed in the gas line connecting the analyzer 18 with the pump 22. Preferred embodiments of the ozone reactor 26 are shown in FIGS. 5A–B. The reactor 26 has a cylindrical body 100 with endcaps 110 at either end. One of the endcaps 110 has an inlet 102 and the other an outlet 104. The body 100 of the reactor and endwalls 110, 111 are made of materials which will not react with ozone. For example, the body 100 could be made of quartz and the endwalls 110, 111 could be graphite ferrules. The reactor 26 is also sealed by any appropriate means to prevent leakage. The interior cavity 106 of the reactor through which the sample gas from the analyzer flows is preferably heated to above about 600 degrees Fahrenheit (°F.), a temperature which sufficient to convert the ozone to non-destructive gases such as oxygen ($O_2$). Thus, the modified sample gas can pass through the pump 22 to the to the exhaust port without causing damage to any of the pump components. The interior of the reactor body 100 can be heated in a number of ways. One preferred method is depicted in FIG. 5A where a heating probe 108 projects into the interior of the reactor body 100 from one end thereof. As most metallic heating probes will react with the ozone, it is preferred that the probe 108 be constructed of a ceramic material, or the like, which will withstand the heat and not react with the ozone. Alternately, a metallic probe having a coating or exterior sheath of a ceramic or like material could be employed. The end of the probe 108 extends from the endwall 110 on the outlet side of the reactor 26 (although it could alternately extent from the other end if desired) into the cavity 106 in a coaxial relationship to the longitudinal axis of the reactor body 100. In this case, the outlet 104 is disposed toward the peripheral edge of the endwall 110 so as to allow room for the probe 108. The probe 108 is energized via a connected power supply (not shown). FIG. 5B illustrates another preferred embodiment for heating the reactor cavity 106. In this embodiment a heating coil 112 is wrapped around the outside of the reactor body 100, as shown, or is alternately embedded within the body 100 (not shown). Here too, the heating coil 112 is energized via a connected power supply (not shown).

Referring once again to FIG. 4, the above-described structure of the reactor 26 can also be employed for another useful purpose. It has been described how nitric oxide is converted to a quantity of nitrogen dioxide so as to avoid its presence being masked by sulfur dioxide. However ammonia, another environmental gas often monitored, is also masked by the sulfur dioxide. Merely mixing the sample with an oxidant such as ozone while it transits through the mixer 14 will not convert ammonia to a gas which is readily detectable. However, if the ammonia first flows through an ammonia reactor 24 having a structure similar to the embodiments of the ozone killer described above (i.e. FIGS. 5A–C), it can be heated to a temperature which causes the ammonia to break down into, among other gases, a quantity of nitric oxide. Specifically, the interior cavity of the reactor 24 through which the sample gas flows would be heated to above about 1000 degrees Fahrenheit (°F.). This temperature will cause the ammonia to break down and the nitric oxide will be formed therefrom. After the ammonia is broken down into nitric oxide, the nitric oxide can be converted to nitrogen dioxide in the mixer 14, and thereafter readily detected by the system 10.

The sample gas can alternately be transmitted through a heated mixer 42 where a reacting agent is also introduced via the heated mixer supply 44. The purpose of this alternate routing is to convert hydrogen sulfide to sulfur dioxide thereby facilitating its detection and quantification, as will be explained below. Preferably, the reacting agent is oxygen ($O_2$) gas, and is introduced at a flow rate of about 50 ml/min. It is believed this flow rate is sufficient to achieve the desired conversion of the maximum amount of hydrogen sulfide that would typically be seen in industrial emissions (i.e. approximately 10 ppm) in the time it takes to pass through the mixer 42, assuming a standard sample gas flow rate of about 300–500 ml/min. The heated mixer 42 can employ the same critical orifice configuration used with the other mixer 14. However, unlike the primary mixer 14, the heated mixer 42 includes a heating unit which is capable of heating the sample, gas passing therethrough to a temperature above about 1000° F. It is the combination of the added oxygen and heat which converts the hydrogen sulfide in the sample gas to a quantity of sulfur dioxide. Both the now modified sample gas and any excess oxygen are then drawn through the spectral analyzer 18 for analysis. As described previously, the absorption characteristics of certain gases, such as hydrogen sulfide, are masked by sulfur dioxide. Thus, when hydrogen sulfide and sulfur dioxide are both present in the gas sample being monitored, it is difficult to detect the presence and quantity of the masked hydrogen sulfide. By converting it to sulfur dioxide, after first having determined the amount of sulfur dioxide originally in the sample gas, it is possible for the processing unit 20 to detect the increase in the sulfur dioxide concentration caused by the conversion process.

Similar to the ammonia and nitric oxide, the sample gas will contain unknown quantities of hydrogen sulfide. Thus, as with the ozone associated with mixer 14, it is preferred that the amount of oxygen provided to the mixer 42 be enough to ensure that even the highest concentrations of hydrogen sulfide are converted to sulfur dioxide. This will likely mean that excess oxygen will be supplied in many cases. This excess oxidant will have a diluting impact on the now modified sample gas, similar to that of the ozone. Here again, the diluting effect of the oxygen can be compensated for via a calibration process, as will now be explained.

It is noted that in some cases, the sample gas will already contain sufficient quantities of oxygen such that the addition of more via the mixer supply 44 is unnecessary. In such cases, the heated mixer 42 would be operated without injecting additional oxygen.

The relationship between the original amount of ammonia, nitric oxide, and/or hydrogen sulfide in the sample gas and the resulting amount of nitrogen dioxide or sulfur dioxide produced from the aforementioned conversion processes is complex and not easily characterized. The spectral analyzer 18 will only disclose how much nitrogen dioxide or sulfur dioxide is present in the modified gas sample. The processing unit 20 must then determine the amounts of nitric oxide and/or ammonia from increases in the nitrogen dioxide content caused by their conversion. Similarly, the amount of hydrogen sulfide must be determined from an increase in the sulfur dioxide content. In addition, the diluting effect of the reacting agent (e.g. ozone or oxygen) must be taken into account when the processing unit 20 determines the concentrations of the environmental gases of interest in the original sample gas. And, the spectral analyzer itself 18 will usually exhibit some small degree of error in its readings.

The processing unit 20 can formulate compensation factors which are employed to determine the original amounts of ammonia, nitric oxide and hydrogen sulfide, and to compensate for the diluent effect of the oxidant and analyzer error, by conducting a series of calibration procedures prior to actual sample gas analysis. To this end the system 10 also includes a calibration unit 28. This calibration unit 28 includes a first gas source 32 containing a calibration gas commonly referred to a zero gas. Zero gas contains none of the gases which are to be detected by the system 10. The calibration unit 28 also includes a one or more additional gas sources 34 each containing a calibration gas which has a known concentration of one of the gases which are to be monitored by the system 10. Each of the gas sources 32, 34 is connected to a calibration gas distribution node 36 which is controlled by the processing unit 20. The distribution node 36 could be a series of individual values each connecting one of the gas sources 32, 34 to a common outlet, or it could be a single multi-position valve with plural inlets individually connectable to a common outlet. In the latter case, each gas supply 32, 34 would be connected to one of the inlets of the multi-position valve. The output of the calibration gas distribution node 36 is connected to one of the inputs of a gas inlet distribution node 30. Here too, the gas inlet distribution node can be a series of interconnected valves or a single multi-position valve with multiple switchable inputs and outputs. The inlet node 30 is also controlled by the processing unit 20. A second input of the gas inlet node 30 is connected to the gas inlet 12 of the system. One output of the inlet node 30 is connected to an inlet of the aforementioned ammonia reactor 24, and another output is connected to the inlet of the heated mixer 42.

Figure 6A:
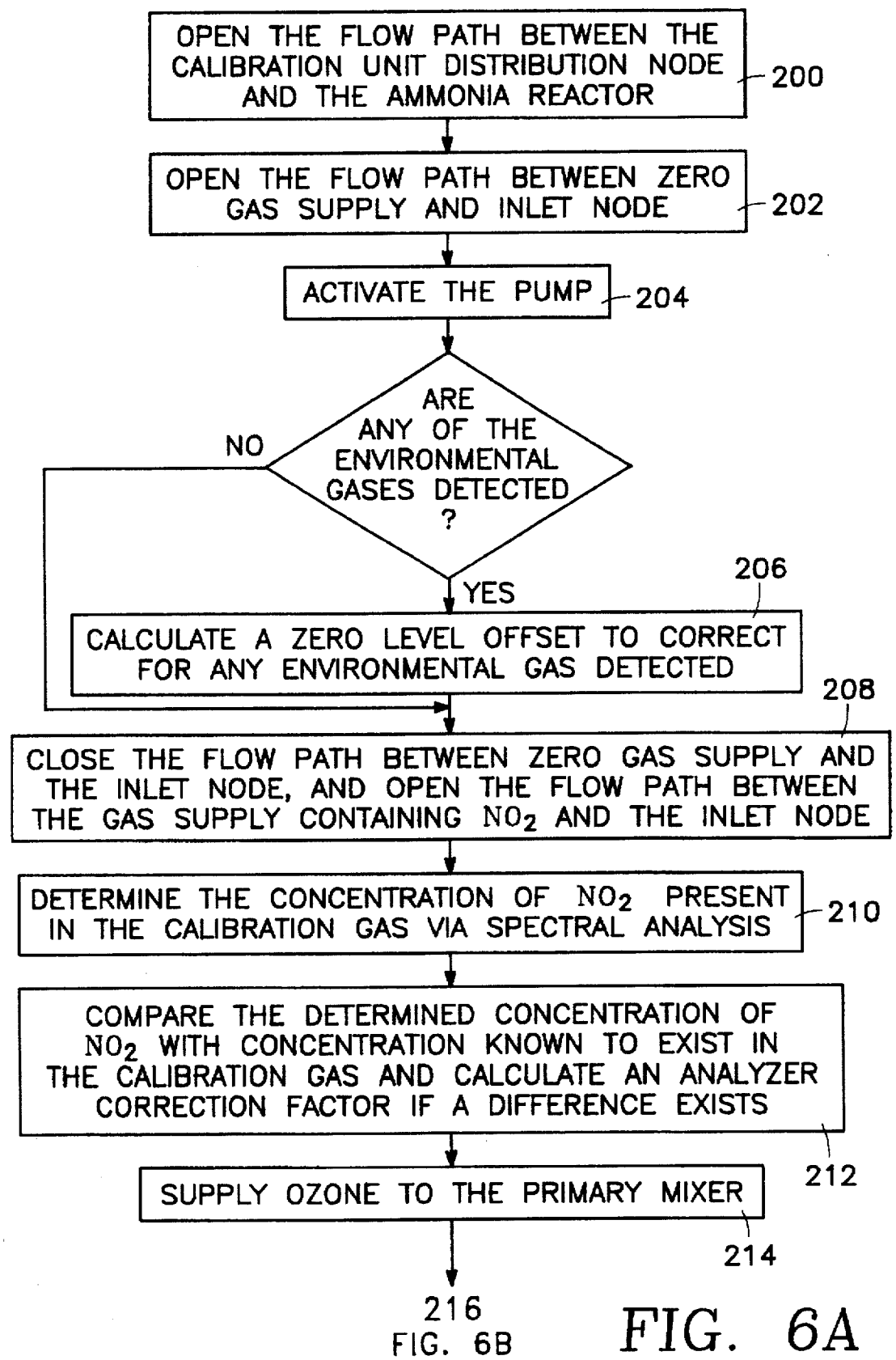
Figure 6C:
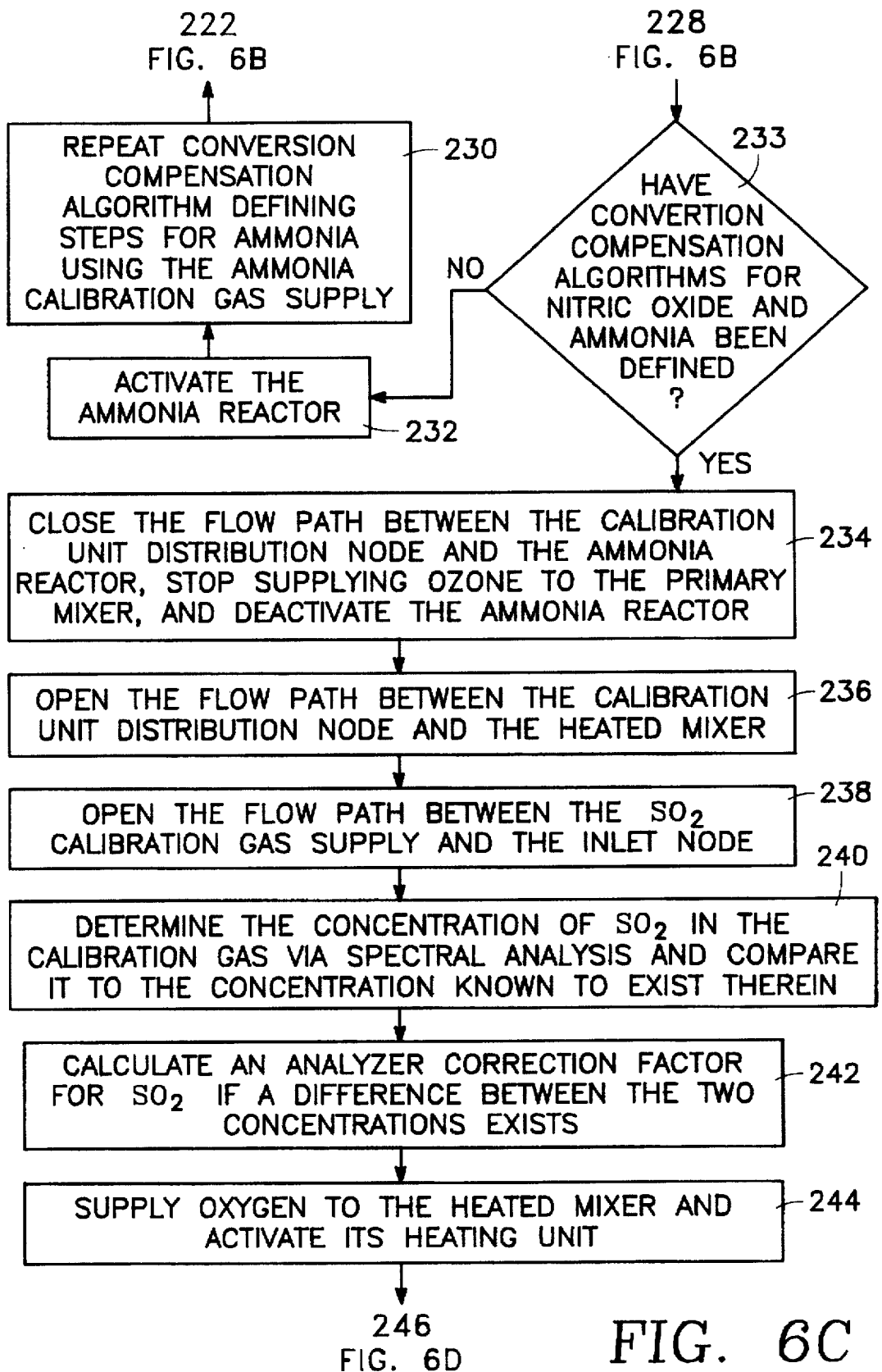
Figure 6D:
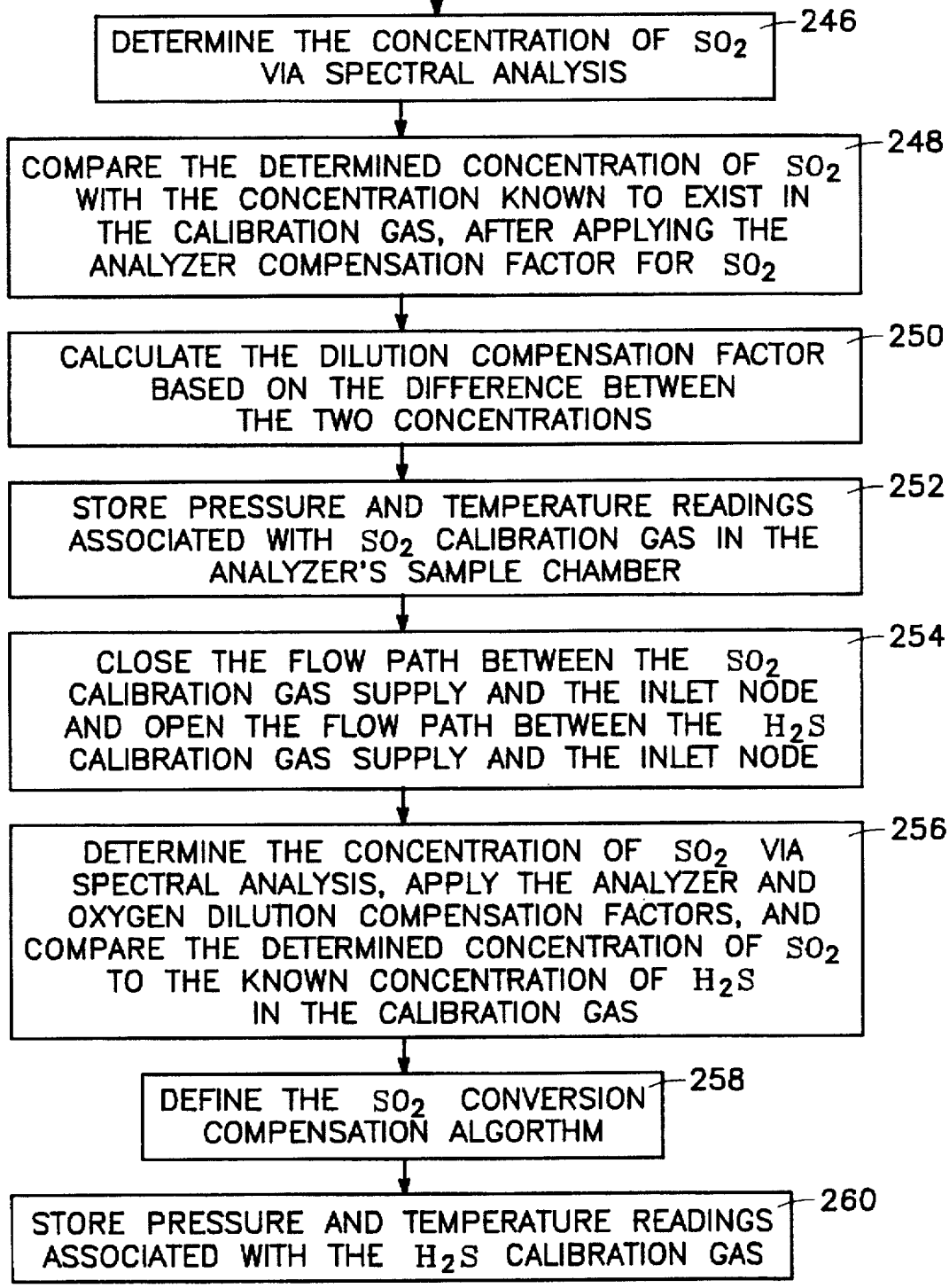

Referring to FIGS. 4 and 6, the preferred calibration process will be explained. During the first step 200 of the calibration procedure for the system 10, the processing unit 20 opens the flow path between the calibration unit's distribution node 36 and the ammonia reactor 24 using the inlet node 30. The processing unit 20 also opens a flow path between the gas supply 32 containing the zero gas and the inlet node 30 using the calibration gas distribution node 36 (step 202). The pump 22, which is also controlled by the processing unit 20, is activated and the zero gas is drawn through the ammonia reactor 24 and mixer 14 into the analyzer 18 (step 204). Since the zero gas lacks any of the gases which are being monitored by the system 10, the resulting signal from the analyzer 18 should indicate their absence. If not, in step 206, the processing unit 20 calculates a zero level offset via well known methods and uses this offset to correct readings from the spectral analyzer 18.

A procedure is then followed to check full scale span calibration of the analyzer 18. This phase of the calibration process has a number of goals. It is used to check the operation of the analyzer 18 itself and to correct for any inaccuracies inherent therein. It is also used to determine the extent of the dilution effect caused by the introduction of a reacting agent into the sample gas, and to compensate for the dilution. And finally, it can be employed to determine, and compensate for, the effects of the conversion process associated with the ammonia, nitric oxide, and hydrogen sulfide. To perform the full scale span check, the processing unit 20 closes the flow path between the zero gas supply 32 and the inlet node 30 and opens a flow path between the gas supply 34 containing a known quantity of nitrogen dioxide and the inlet node 30, using the calibration gas distribution node 36 (step 208). Preferably, this known quantity is approximately equal to the maximum anticipated concentration of nitrogen dioxide in the sample gas. The same is true of all the other calibration gases containing nitric oxide, ammonia, sulfur dioxide, or hydrogen sulfide. In step 210, the processing unit 20 determines the concentration of the nitrogen dioxide present in the calibration gas via spectral analysis. This determined concentration of nitrogen dioxide is then compared to the concentration known to exist in the calibration gas. Any difference between the two concentrations is due to inaccuracy in the spectral analyzer 18. If a difference does exist, the processing unit 20 calculates a correction factor for nitrogen dioxide in accordance with well known methods (step 212).

In the next step 214, ozone is supplied to the mixer 14, even though it is not needed to convert nitric oxide. In this way, the aforementioned diluting effect of the ozone can be detected by comparing the concentration of nitrogen dioxide derived from the spectral analysis and the amount known to be in the calibration gas (step 216). Of course, any inaccuracies in the spectral analyzer are also part of this difference, therefore, the previously-calculated analyzer correction factor for nitrogen dioxide must be applied to the derived concentration before comparing it to the known concentration of the calibration gas. The processing unit 20 next calculates a compensation factor for ozone dilution using the difference between the derived and actual concentrations of nitrogen dioxide (step 218).

The process by which the calibration gases containing either ammonia or nitric oxide are used is somewhat different that that for the nitrogen dioxide calibration gas because of the additional effects of their conversion in the ammonia reactor 24 and mixer 14. Although the dilution effect is substantially constant regardless of the amounts of ammonia or nitric oxide in the original sample gas and can be applied to any result, the amount of nitrogen dioxide produced from these gases will vary depending on their concentrations in the original sample gas. Accordingly, conversion compensation algorithms must be derived to determine the true amount of ammonia and nitric oxide in the sample gas.

The system is calibrated for nitric oxide by first closing the flow path between the inlet node 30 and the calibration gas supply 34 containing the nitrogen dioxide, while opening the flow path between the inlet node 30 and the calibration gas supply 34 containing nitric oxide (step 222). The algorithm required to determine the concentration of nitric oxide based on the concentration of nitrogen dioxide produced via the conversion process is well known in the analyzer art and are essentially polynomial equations. The scaling factors associated with the algorithm are derived from the difference between the concentration of nitrogen dioxide created by the conversion process and the concentration of nitric oxide known to exist in the gas, after the previously-derived factors associated the dilution effect and analyzer inaccuracy has been applied. This is accomplished by determining the concentration of nitrogen dioxide via spectral analysis, applying the analyzer and dilution compensation factors to determine the actual concentration of nitrogen dioxide, and finally comparing the determined concentration of nitrogen dioxide with the known concentration of nitric oxide in the calibration gas (step 224). The compensation algorithm derived for the nitric oxide is defined once the aforementioned difference is determined (step 226). The same process is repeated using a calibration gas containing ammonia to define an ammonia conversion compensation algorithm (step 230), except that the processing unit 20 also activates the ammonia reactor 24 (step 232) during the callibration process. The compensation algorithms are used to calculate the true concentration of ammonia and nitric oxide from the analyzer readings. For example, the compensation algorithm derived for nitric oxide can be applied to any amount of nitrogen dioxide determined to be in the modified sample gas as a result of the conversion of nitric oxide to arrive at a true concentration of the gas (assuming of course that the compensation factors for the dilution effect and analyzer inaccuracy are applied first). The same type of calculation can be made to determine the true amount of ammonia in the original sample gas using the derived ammonia oxide compensation algorithm.

The next phase of the calibration process determines a compensation factor to account for the dilution effect of the oxygen introduced in the heated mixer 42 (and any inaccuracies inherent in the spectral analyzer 18), as well as calibrating the system 10 for sulfur dioxide and hydrogen sulfide. In step 234, the processing unit 20 closes the flow path between the calibration unit distribution node 36 and the ammonia reactor 24, stops the flow of ozone to the primary mixer 14, and deactivates the ammonia reactor 24. The processing unit 20 then opens the flow path between the calibration unit distribution node 36 and the heated mixer 42 (step 236), while at the same time opening the flow path between the sulfur dioxide calibration gas supply 34 and the inlet node 30 (step 238). In step 240, the processing unit 20 determines the concentration of sulfur dioxide via spectral analysis and compares this to the actual concentration present in the calibration gas. Any difference is attributable to inaccuracy in the spectral analyzer and a correction factor is calculated for sulfur dioxide readings (step 242). Next, the processing unit 20 causes oxygen to be supplied to the heated mixer 42, and activates the mixer's heating unit (step 244). The processing unit 20 then determines the concentration of sulfur dioxide in the calibration gas (step 246). Next, in step 248, the concentration of sulfur dioxide derived by spectral analysis is compared with that known to exist in the calibration gas, after first applying the analyzer correction factor to the derived sulfur dioxide concentration. And finally, the oxygen dilution factor associated with the heated mixer 42 is calculated based on the difference between the two concentrations (step 250).

Finally, the system is calibrated for hydrogen sulfide by first closing the flow path between the inlet node 30 and the calibration gas supply 34 containing the sulfur dioxide, while opening the flow path between the inlet node 30 and the calibration gas supply 34 containing hydrogen sulfide (step 254). Here too, algorithms needed to determine the concentration of the hydrogen sulfide in the sample gas are well known in the analyzer art, and are defined in a way similar to the process used for ammonia and nitric oxide. Namely, the algorithm is developed by determining the difference between the concentration of sulfur dioxide derived from spectral analysis of the converted calibration gas once containing hydrogen sulfide and the concentration of hydrogen sulfide known to have originally existed in the gas, after the previously-derived factor associated the oxygen dilution effect and analyzer inaccuracy has been applied (step 256). The compensation algorithm derived for the hydrogen sulfide is defined once the aforementioned difference is determined (step 258) using well known methods. Once defined, the compensation algorithm can be used to calculate the true concentration of the gas from the analyzer readings of the sample gas. For example, the compensation algorithm derived for hydrogen sulfide can be applied to any amount of sulfur dioxide determined to be in a modified sample gas as a result of the conversion of hydrogen sulfide during actual monitoring operations to arrive at a true concentration of the gas in the original sample gas (assuming of course that the compensation factor for the oxidant dilution effect is applied first).

If however, the sample gas already contains sufficient amounts of oxygen as discussed previously, no additional oxygen would be supplied to the heated mixer 42. Accordingly, there is no need to calculate a dilution compensation factor for the oxygen, and steps 244, 246, 248, and 250 can be eliminated. In addition, no dilution factor need be applied in step 256 to calculate the compensation algorithm for hydrogen sulfide.

A spectroscopic gas analyzer typically measures the absorption of light across a spectrum to determine the concentration of certain gases in a sample gas. The absorption, however, is related to the number of gas molecules in the sample chamber of the spectral analyzer. Temperature and pressure affect the number of molecules present in the chamber in accordance with well known gas laws. Thus, both pressure and temperature must be taken into consideration when determining the true concentrations of an environmental gas of interest within the sample gas being monitored.

The pressure of the modified sample gas within the sample chamber of the spectral analyzer 18 during the monitoring operation will depend on many factors, such as the pressure of the sample gas when it was introduced into the system 10, the efficiency of the pump 22, as well as the ambient atmospheric pressure at the time of the monitoring. If the pressure of the sample gas in the analyzer's sample chamber during gas monitoring operations for a particular gas is different from the pressure in the chamber at the time the system was calibrated for that gas, the results of the spectral analysis will be skewed. Therefore, it is important to determine if the chamber pressure has varied from that exhibited in the calibration procedure during actual monitoring operations. This task is accomplished by including a pressure sensor 38 in the spectral analyzer 18 which provides a readout to the processing unit 20 indicating the absolute pressure of the gas within the analyzer's sample chamber. Referring once again to FIG. 6, during the full scale span calibration of each environmental gas of interest, the processing unit 20 stores the pressure reading associated with that test (see steps 220, 228, 252, and 260). Subsequently, during monitoring operations, the processing unit 20 compares the then current pressure reading with the stored reading to determine if a difference exists. If a difference does exist, the concentration of the gas calculated by the processing unit 20 as described above is adjusted to compensate for any change in the pressure. This compensation is accomplished using algorithms well known in the gas analyzer art.

A similar process is preferably employed to compensate for any variation in the temperature of the sample gas within the analyzer's sample chamber. To this end, the a temperature sensor 40 is include in the spectral analyzer 18 which is capable of providing an signal to the processing unit 20 indicative of the temperature of a gas in the chamber. The temperature associated with each calibration gas analyzed during the full scale span calibration phase is stored by the processing unit 20 (see steps 220, 228, 252, and 260 in FIG. 6). This stored temperature for an environmental gas is then compared with the temperature exhibited by the sample gas during actual monitoring operations for that environmental gas. If there is a difference between these two temperatures, the processing unit modifies the calculated concentration of the gas to compensate for the change in temperature. Here too, the algorithms employed to accomplish the modification process are well known in the gas analyzer art.

Emissions being monitored for environmental gases may contain ammonia, nitric oxide, nitrogen dioxide, hydrogen sulfide, and sulfur dioxide in varying concentrations. Emission monitoring application typically require one or more of these gases to be detected and quantified. As an example of how the gas analyzer system according to the present invention can be adapted to provide this information, the following paragraphs will describe preferred processes for detecting and quantifying all of the above-listed gases. Of course, if any of these gases are not of interest, the steps associated with the analysis thereof could simply be eliminated to streamline the procedure and reduce processing time.

Figure 7A:
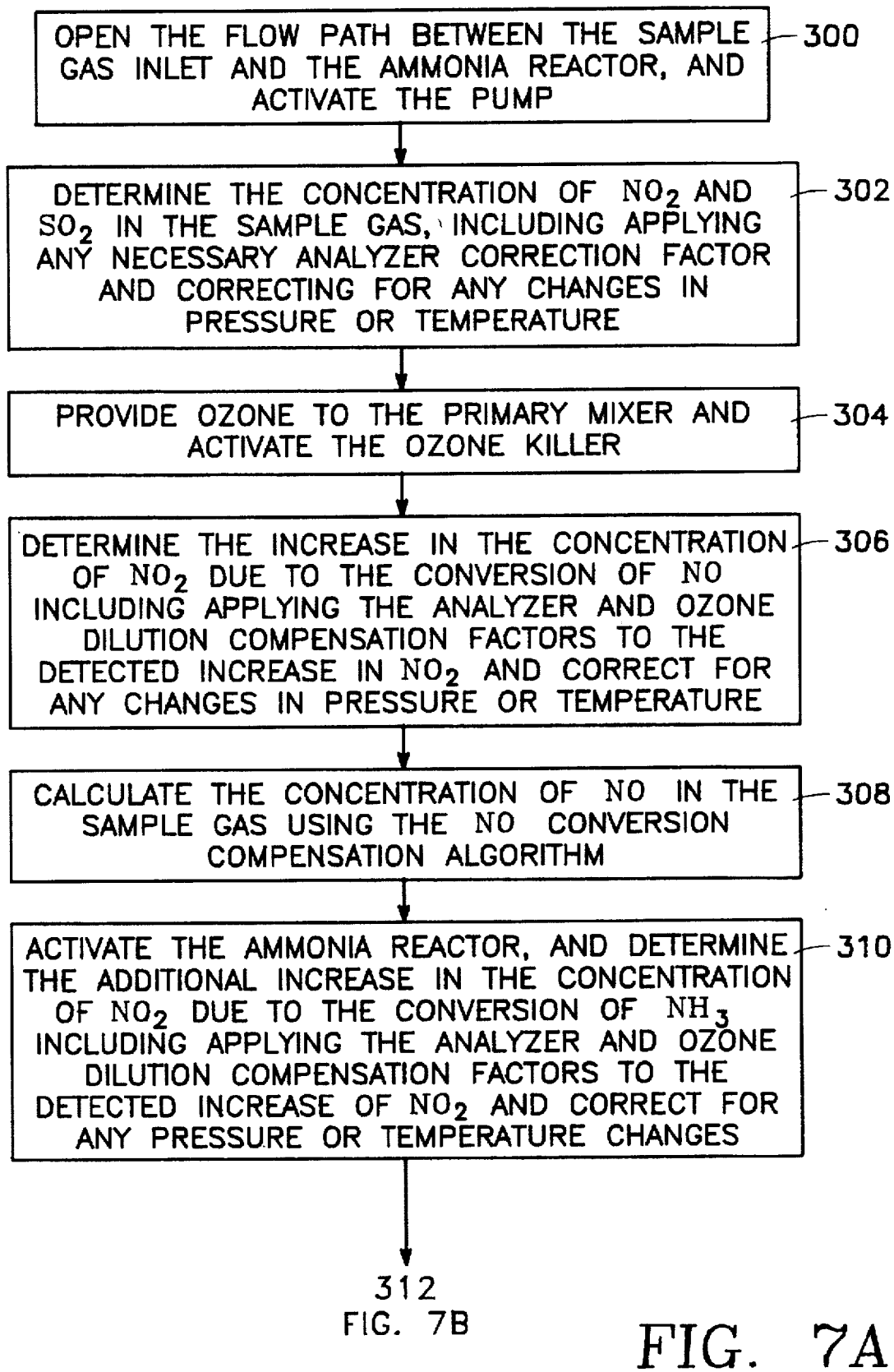
FIGS. 7A and 7B are block diagrams showing a method for determining the concentrations of nitrogen dioxide, nitric oxide, ammonia, sulfur dioxide, and hydrogen sulfide in a sample gas using the system of FIG. 4.
Figure 7B:
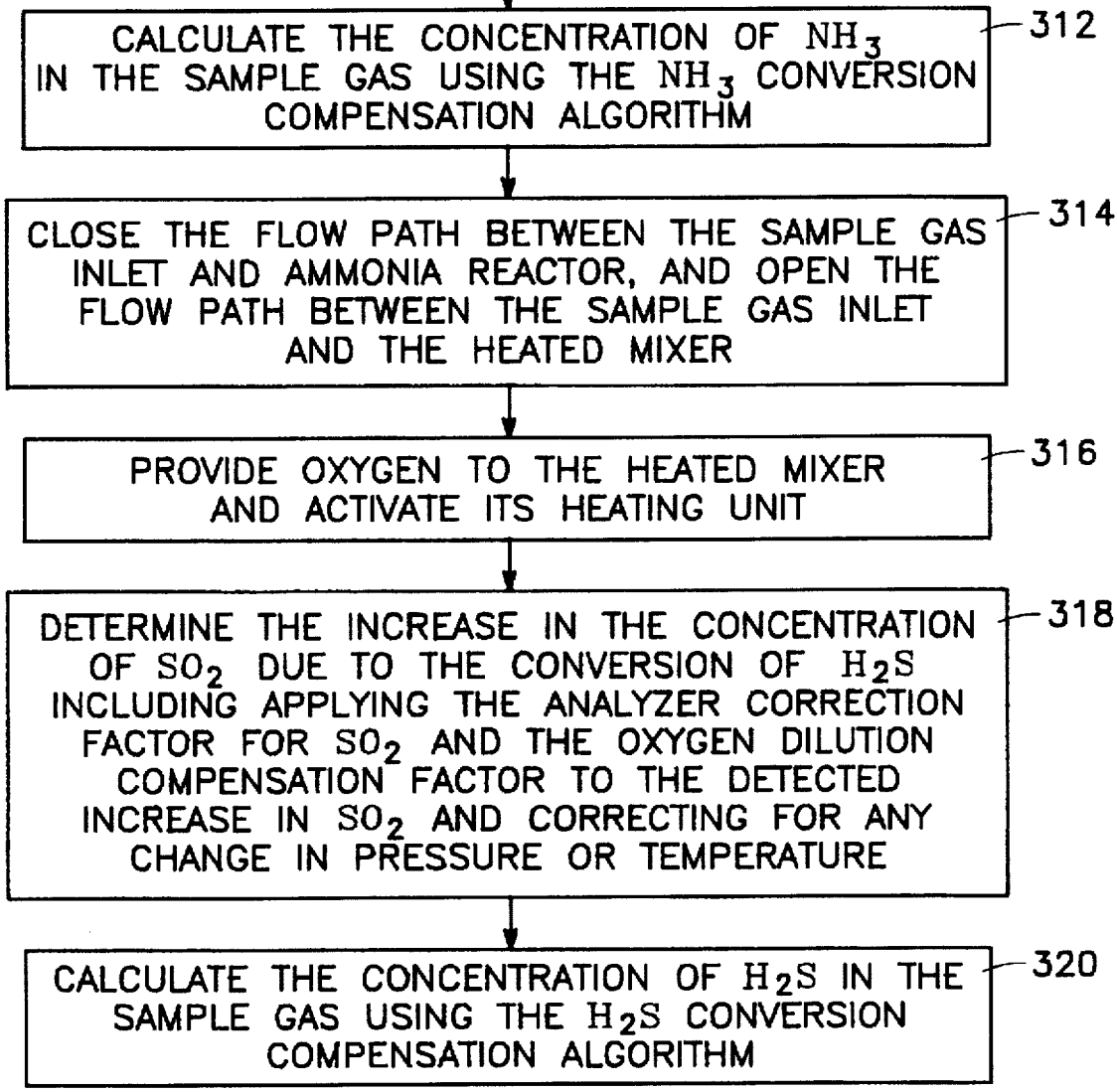

A first way of accomplishing the monitoring task would be for the processing unit 20 to, in an initial step 300 shown in FIG. 7, open the flow path between the sample gas inlet 12 and the ammonia reactor 24, and activate the pump 22. The flow path to the heated mixer 42 would be kept closed. The results of the ensuing spectral analysis would be used to determine the concentration of nitrogen dioxide and sulfur dioxide respectively present in the sample gas (step 302). This step would include applying any analyzer correction factor required for either gas, and correcting for any changes in the pressure or temperature in the analyzers sample chamber in comparison to when the system was calibrated for nitrogen dioxide and sulfur dioxide, respectively. In step 304, the processing unit 20 would then provide ozone to the mixer 14, and activate the ozone killer 26 to prevent damage to the pump 22. Next, the increase in the concentration of nitrogen dioxide in the modified sample gas caused by the conversion of nitric oxide is determined (step 306). In making this determination, the analyzer correction factor associated with nitrogen dioxide and the ozone dilution compensation factor would be applied to the increase to correct for any analyzer inaccuracy and the dilution effect of the ozone. In addition, the increased concentration reading would be corrected for any changes in the pressure or temperature in the analyzer's sample chamber in comparison to when the system was calibrated for nitric oxide. The processing unit 20 next calculates the actual concentration of nitric oxide in the sample gas by applying the compensation algorithm for nitric oxide to the aforementioned derived increase in the nitrogen dioxide level (step 308). The processing unit 20 would then activate the ammonia reactor 24, as well as continuing to provide ozone to the mixer 14 (step 310). The results of this step would be a further increase in the concentration of nitrogen dioxide detected in the spectral analysis. This additional increase would correspond to the amount of ammonia in the sample. Similar to the last step, this step of the process includes application of the analyzer and ozone dilution compensation factors to the increase in the nitrogen dioxide level associated with the conversion of ammonia so as to correct for any analyzer inaccuracy associated with the analysis of nitrogen dioxide and for the dilution effect of the ozone. The step also includes correcting the increase concentration reading for any changes in the pressure or temperature in the analyzer's sample chamber in comparison to when the system was calibrated for ammonia. The processing unit 20 then calculates the actual concentration of ammonia in the sample gas by applying the compensation algorithm for ammonia to the increase in the nitrogen dioxide level (step 312). In step 314, the processing unit 20 would close the flow path through mixer 14, and open the flow through heated mixer 42. The processing unit 20 would then provide oxygen to the mixer 42 and activate its heater (step 316). The results of this step would show an increase in the concentration of sulfur dioxide corresponding to the conversion of hydrogen sulfide. The increase in the concentration of sulfur dioxide would then be determined (step 318). This would include applying the analyzer correction factor for sulfur dioxide, applying the oxygen dilution compensation factor (if necessary), and correcting for any changes in the pressure or temperature in the analyzer's sample chamber in comparison to when the system was calibrated for hydrogen sulfide. Finally, in step 320 the concentration of hydrogen sulfide in the sample gas is calculated using the compensation algorithm derived for hydrogen sulfide during calibration of the system.

This above-described sequentially stepped process can Be accomplished in a relatively short period of time (i.e. quick enough to meet the aforementioned one sample per minute analysis rate) due to the real time conversion of nitric oxide, ammonia, and hydrogen sulfide. However, if it is anticipated that the concentrations of the nitrogen and sulfur containing gases may vary significantly over the analysis period, the process may not provide satisfactory results. Although this situation is rare, it is possible to provide real time monitoring for every gas simultaneously by employing plural separate systems (in this case four), preferably all sharing a common processing unit. A sample of the gas being monitored would be directed to all the systems. In the first system, the ammonia reactor 24 and mixers 14, 42 would be deactivated (or eliminated if desired). This system would provide an indication of the concentration of nitrogen dioxide and sulfur dioxide in the sample gas. The second system would include an active mixer 14, but its ammonia reactor 24 and mixer 42 (if present) would be deactivated. The second system would be used to indicate the then increased concentration of nitrogen dioxide corresponding to the conversion of nitric oxide. A third system would have both an active ammonia reactor 24 and mixer 14, but an inactive mixer 42 (if present). This third system would provide an indication of the increased concentration of nitrogen dioxide associated with the conversion of both ammonia and nitric oxide. A final system would have an active heated mixer 42, but the ammonia reactor 24 and mixer 14 would be inactivated (or eliminated). This last system would be used to indicate the increased concentration of sulfur dioxide caused by the conversion of hydrogen sulfide in the sample gas. The processing unit 20 would be programmed to compare the spectral analysis results from the four systems and calculate the individual concentration of all three nitrogen-containing gases, as well as the concentrations of sulfur dioxide and hydrogen sulfide.

Many environmental gas monitoring application do not require that the concentrations of each of the aforementioned nitrogen-containing gases (i.e. nitrogen dioxide, nitric oxide, and ammonia). Rather, a total quantity of nitrogen-containing gases is desired. In such cases, the processing unit 20 would calculate a combined concentration from the individual concentrations calculated previously. It is also sometimes required that a total concentration of NOX gases (i.e. nitrogen dioxide and nitric oxide) be provided. Here again, this information can be given by combining the individually derived concentrations for these gases.

While the invention has been described in detail by reference to the preferred embodiment described above, it is understood that variations and modifications thereof may be made without departing from the true spirit and scope of the invention. For example, the above-described system was employed to monitor industrial emission for specific environmental gases, i.e. nitrogen dioxide, ammonia, nitric oxide, sulfur dioxide, and hydrogen sulfide. However, the invention is not limited to this application, or to the environmental gases listed. Rather, the system according to the present invention could be employed for any gas analysis application, and for many different gases, while still enjoying all its novel advantages. For instance, the mixers (i.e.

primary and heated) would be available to convert gases which are masked by others to more detectable species using the appropriate reacting agent.

Wherefore, what is claimed is:

1. A gas analyzer system, comprising:

a sample gas inlet for introducing a sample gas which is to be analyzed;

a first mixer having a first inlet into which the sample gas can be fed and an outlet;

a first mixer supply containing an oxidant gas connected to a second inlet of the first mixer so as to supply the oxidant gas thereto, said oxidant gas capable of being supplied to the first mixer in a sufficient quantity to convert substantially all of a quantity of nitric oxide (NO) present in the sample gas to a gas comprising a quantity of nitrogen dioxide ($NO_2$), said conversion taking place in the time it takes for the sample gas to flow through the first mixer;

an ammonia reactor disposed between the sample gas inlet and the first mixer, said ammonia reactor being capable of converting gaseous ammonia to a gas comprising a quantity of nitric oxide in the time it takes for the sample gas to flow through the ammonia reactor;

a second mixer having a first inlet into which the sample gas can be fed and an outlet, said second mixer being employed to convert substantially all of a quantity of hydrogen sulfide ($H_2S$) present in the sample gas to sulfur dioxide ($SO_2$) in the time it takes for the sample gas to flow through the second mixer;

an inlet distribution node having a first inlet connected to the sample gas inlet, a first outlet connected to an inlet of the ammonia reactor, and a second outlet connected to the first inlet of the second mixer, said inlet distribution node being capable of exclusively routing the sample gas to either the ammonia reactor or the second mixer;

a processing unit capable of controlling the inlet distribution node so as to cause the node to route the sample gas to either the ammonia reactor or the second mixer; and a spectral analyzer having an inlet connected to the first mixer outlet and the second mixer outlet, and into which the sample gas is capable of being fed, said spectral analyzer further being capable of outputting a signal indicative of a radiation intensity spectrum over a range of wavelengths associated with the sample gas;

a pump having an inlet connected to an outlet of the spectral analyzer, said pump being capable of transporting the sample gas through the gas analyzer system.

2. The system of claim 1, wherein the ammonia reactor comprises:

a housing having a longitudinal chamber;

an inlet on one end of the chamber and an outlet on the other end of the chamber; and means for heating gases flowing through the longitudinal chamber.

3. The system of claim 2, wherein the heating means of the ammonia reactor comprises one of (i) a heating probe extending into the longitudinal chamber from an internal wall of the housing, and (ii) a heating coil wrapped around the longitudinal chamber over at least a portion of its length.

4. The system of claim 2, wherein the heating means of the ammonia reactor is capable of heating gases flowing through the longitudinal chamber to a temperature exceeding about 1000 degrees Fahrenheit.

5. The system of claim 1 further comprising a second mixer supply containing an oxidant gas connected to a second inlet of the second mixer so as to supply oxidant gas thereto, said oxidant gas being supplied to the mixer in a sufficient quantity to facilitate said conversion of substantially all of a quantity of hydrogen sulfide ($H_2S$) present in the sample gas to sulfur dioxide ($SO_2$) in the time it takes for the sample gas to flow through the second mixer.

6. The system of claim 5 wherein the oxidant gas supplied to the second mixer is oxygen.

7. The system of claim 1 wherein the second mixer is capable of heating gases flowing therethrough to a temperature exceeding approximately 1000 degrees Fahrenheit.

8. The system of claim 1, wherein said processing unit is further capable of detecting the presence and determining the concentration of nitrogen dioxide, nitric oxide, ammonia, sulfur dioxide, and hydrogen sulfide gases in the sample gas from the signal output by the spectral analyzer.

9. The system of claim 1, further comprising a calibration unit connected to a second inlet of the inlet distribution node, said calibration unit being capable of supplying a plurality of different calibration gases to the inlet distribution node and wherein said inlet distribution node is capable of exclusively routing the calibration gases to either the ammonia reactor or the second mixer.

10. The system of claim 9 wherein the calibration unit further comprises:

a plurality of gas supplies each containing one of said plurality of calibration gases; and a calibration unit distribution node having a plurality of inlets each of which is connected to one of the plurality of gas supplies, and an outlet connected to the second inlet of the inlet distribution node, said calibration unit distribution node being capable of exclusively routing each one of the calibration gases to the inlet distribution node.

11. The system of claim 10 wherein said processing unit is further capable of controlling the calibration unit distribution node so as to cause the calibration unit distribution node to route the calibration gases to the inlet distribution node, and to cause the inlet distribution node to route one of the sample gas or the calibration gases to either the ammonia reactor or the second mixer.

12. The system of claim 9 wherein said plurality of calibration gases comprises a zero gas and at least one gas having a predetermined concentration of a single environmental gas, said environmental gas being one of (i) nitrogen dioxide, (ii) nitric oxide, (iii) ammonia, (iv) sulfur dioxide, and (v) hydrogen sulfide.

13. The system of claim 12 wherein the concentration of the environmental gas in the calibration gas is approximately the maximum concentration of that environmental gas expected to be present in the sample gas.

14. The system of claim 1 wherein the oxidant gas supplied to the first mixer is ozone.

15. The system of claim 14, wherein the ozone is capable of causing damage to the pump, and wherein the system further comprises an ozone killer capable of converting the ozone to gases which will not damage the pump, said ozone killer being connected between the spectral analyzer and the pump.

16. The system of claim 15, wherein the ozone killer comprises:

a housing having a longitudinal chamber;

an inlet on one end of the chamber and an outlet on the other end of the chamber; and means for heating gases flowing through the longitudinal chamber.

17. The system of claim 16 wherein the heating means of the ozone killer comprises one of (i) a heating probe extending into the longitudinal chamber from an internal wall of the housing, and (ii) a heating coil wrapped around the longitudinal chamber over at least a portion of its length.

18. The system of claim 16 wherein the heating means of the ozone killer is capable of heating gases flowing through the longitudinal chamber to a temperature exceeding about 600 degrees Fahrenheit.

19. The system of claim 1, further comprising a pressure sensor capable of sensing the absolute pressure within a sample chamber of the spectral analyzer and outputting a signal indicative of the absolute pressure to a processing unit.

20. The system of claim 1, further comprising a temperature sensor capable of sensing the temperature of gases within a sample chamber of the spectral analyzer and outputting a signal indicative of the temperature to a processing unit.

21. The system of claim 1, wherein the spectral analyzer is a diode-array spectrophotometer.

22. A gas reactor, comprising:
- a housing comprising a hollow cylindrical body section constructed of quartz forming a longitudinal chamber within;
- an inlet on one end of the chamber and an outlet on the other end of the chamber, wherein the inlet comprises a graphite ferule with through hole to allow passage of gas therethrough and the outlet comprises a graphite ferule with through hole to allow passage of gas therethrough; and
- means for heating gases flowing through the longitudinal chamber.

23. The gas reactor of claim 22, wherein the heating means of the gas reactor comprises one of (i) a heating probe extending into the longitudinal chamber from an internal wall of the housing, and (ii) a heating coil wrapped around the longitudinal chamber over at least a portion of its length.

24. The gas reactor of claim 23 wherein the heating probe comprises a ceramic material.

25. The gas reactor of claim 23 wherein the heating probe comprises an inner portion, and an outer portion which encases the inner portion, and wherein the outer portion comprises a ceramic material.

26. The gas reactor of claim 22 wherein:
- the heating means of the gas reactor is capable of heating gases flowing through the longitudinal chamber to a temperature exceeding about 600 degrees Fahrenheit; and
- the gas reactor is an ozone killer capable of converting ozone present in a gas flowing through the longitudinal chamber to a gas comprising oxygen, said conversion of the ozone resulting from heating the gas flowing through the chamber to a temperature exceeding about 600 degrees Fahrenheit.

27. The gas reactor of claim 22 wherein:
- the heating means of the gas reactor is capable of heating gases flowing through the longitudinal chamber to a temperature exceeding about 1000 degrees Fahrenheit; and
- the gas reactor is an ammonia reactor capable of converting ammonia present in a gas flowing through the longitudinal chamber to a gas comprising nitric oxide, said conversion of the ammonia resulting from heating the gas flowing through the chamber to a temperature exceeding about 1000 degrees Fahrenheit.

28. A method of spectroscopic gas analysis, comprising the steps of:
- introducing a sample gas for analysis into a sample gas inlet of a spectroscopic gas analyzer system;
- feeding the sample gas from the sample gas inlet into one of (i) an ammonia reactor to convert gaseous ammonia to a gas comprising a quantity of nitric oxide in the time it takes for the sample gas to flow through the ammonia reactor, or (ii) a first mixer to convert substantially all of a quantity of hydrogen sulfide ($H_2S$) present in the sample gas to sulfur dioxide ($SO_2$) in the time it takes for the sample gas to flow through the first mixer;
- whenever the sample gas is fed into the ammonia reactor, feeding it thereafter into a second mixer and simultaneously supplying an oxidant gas to the second mixer, said oxidant gas being supplied to the second mixer in a sufficient quantity to convert substantially all of a quantity of nitric oxide (NO) present in the sample gas to a gas comprising a quantity of nitrogen dioxide ($NO_2$), said conversion taking place in the time it takes for the sample gas to flow through the second mixer;
- feeding sample gas from the first mixer and sample gas from the second mixer to the spectral analyzer, said spectral analyzer outputting a signal indicative of a radiation intensity spectrum over a range of wavelengths associated with the sample gas.

29. The method of claim 28 further comprising the step of whenever the sample gas is fed into the first mixer, simultaneously supplying an oxidant gas to the first mixer, said oxidant gas being supplied to the first mixer in a sufficient quantity to facilitate said conversion of substantially all of a quantity of hydrogen sulfide ($H_2S$) present in the sample gas to sulfur dioxide ($SO_2$) in the time it takes for the sample gas to flow through the first mixer.

30. The method of claim 28, further comprising the step of detecting the presence and determining the concentration of nitrogen dioxide, nitric oxide, ammonia, sulfur dioxide, and hydrogen sulfide gases in the sample gas from the signal output by the spectral analyzer.

31. The method of claim 28, wherein the oxidant gas supplied to the second mixer is ozone which is capable of causing damage to a pump employed to fed the sample gas through the spectroscopic gas analyzer system, said method further comprising the step of converting the ozone to gases which will not damage the pump prior to the sample gas reaching the pump.

* * * * *

UNITED STATES PATENT AND TRADEMARK OFFICE
CERTIFICATE OF CORRECTION

PATENT NO. : 5,739,038
DATED       : April 14, 1998
INVENTOR(S) : Burrows

It is certified that error appears in the above-identified patent and that said Letters Patent is hereby corrected as shown below:

In Column 4, line 8, please replace "an reading" with ---a reacting---

<div align="right">

Signed and Sealed this

Eighth Day of September, 1998

BRUCE LEHMAN

*Commissioner of Patents and Trademarks*

</div>

*Attest:*

*Attesting Officer*